(12) United States Patent
Sawada et al.

(10) Patent No.: US 8,476,438 B2
(45) Date of Patent: Jul. 2, 2013

(54) PROCESS FOR PRODUCTION OF CAMPTOTHECIN DERIVATIVE

(75) Inventors: Seigo Sawada, Tokyo (JP); Takashi Yaegashi, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 1153 days.

(21) Appl. No.: 12/226,506

(22) PCT Filed: Apr. 27, 2007

(86) PCT No.: PCT/JP2007/059155
§ 371 (c)(1),
(2), (4) Date: Jan. 13, 2009

(87) PCT Pub. No.: WO2007/126046
PCT Pub. Date: Nov. 8, 2007

(65) Prior Publication Data
US 2012/0142926 A1 Jun. 7, 2012

(30) Foreign Application Priority Data
Apr. 27, 2006 (JP) ................................. 2006-123816

(51) Int. Cl.
*C07D 471/00* (2006.01)
(52) U.S. Cl.
USPC ........................................................ 546/48
(58) Field of Classification Search
USPC ........................................................ 546/48
See application file for complete search history.

(56) References Cited

U.S. PATENT DOCUMENTS

| 4,399,282 A | 8/1983 | Miyasaka et al. |
| 4,473,692 A | 9/1984 | Miyasaka et al. |
| 6,476,225 B2 * | 11/2002 | Sobotta et al. ................. 546/48 |
| 2002/0111489 A1 | 8/2002 | Sobotta et al. |
| 2004/0087609 A1 | 5/2004 | Yaegashi et al. |

FOREIGN PATENT DOCUMENTS

| JP | 62-42914 B2 | 9/1987 |
| JP | 62-47193 B2 | 10/1987 |
| JP | 64-061482 A | 3/1989 |
| JP | 3-68007 B2 | 10/1991 |
| JP | 2004-521909 A | 7/2004 |
| WO | WO 01/70747 A1 | 9/2001 |
| WO | WO 02/064597 A2 | 8/2002 |

OTHER PUBLICATIONS

Bach et al. Organic Syntheses, Coll. vol. 7, p. 126 (1990); vol. 60, p. 63 (1981).*
Dorwald F. A. Side Reactions in Organic Synthesis, 2005, Wiley: VCH, Weinheim p. IX of Preface p. 1-15.*
Li, Y. et al., Improving synthetic Method of Irinotecan. Chinese Journal of Medicinal Chemistry, 4(11):238-240 (2001).
Aiyama, R. et al., "A Camptothecin Derivative from Nothapodytes Foetida," *Phytochemistry* 1998; 27(11): 3663-3664.
Sawada, S. et al., "Synthesis and Antitumor Activity of 20(S)-Camptothecin Derivatives: Carbamate-Linked, Water-Soluble Derivatives of 7-Ethyl-10-hydroxycamptothecin," *Chem. Pharm. Bull.* 1991; 39(6): 1446-1454.

* cited by examiner

*Primary Examiner* — Nizal Chandrakumar
(74) *Attorney, Agent, or Firm* — Wolf, Greenfield & Sacks, P.C.

(57) ABSTRACT

Disclosed is a process for production of 7-ethyl-10-[4-(1-piperidino)-1-piperidino]-carbonyloxycamptothecin from a camptothecin composition containing 18,19-dehydrocamptothecin without producing any vinyl form of the compound. The process is characterized by catalytically reducing at least one compound selected from a compound (1) and others in the process of producing a compound (5) from a composition containing the compound (1).

6 Claims, No Drawings

PROCESS FOR PRODUCTION OF CAMPTOTHECIN DERIVATIVE

RELATED APPLICATIONS

This application is a national stage filing under 35 U.S.C. §371 of PCT International application PCT/JP2007/059155, filed Apr. 27, 2007.

TECHNICAL FIELD

The present invention relates to a process for preparing 7-ethyl-10-[4-(1-piperidino)-1-piperidino]carbonyloxy-camptothecin and its derivatives.

BACKGROUND ART

Camptothecin (hereinafter, referred to as CPT) is a pentacyclic alkaloid isolated from natural materials such as *Camptotheca acuminata*, Nyssaceae, which is native to China. Various effective semi-synthetic derivatives having anti-tumor activity prepared using CPT as a starting material have been provided from searching studies by the present inventors and others.

CTP-11, which is a hydrochloride trihydrate of 7-ethyl-10-[4-(1-piperidino)-1-iperidino]carbonyloxycamptothecin (hereinafter, referred to as SN-38B-11) derivatized from CPT, is a compound having high anti-tumor activity with low toxicity, and CPT-11 is widely sold as an anti-tumor agent (general name: irinotecan hydrochloride) at present.

However, since the amount of CPT that can be obtained from a natural material such as *Camptotheca acuminata*, which is a raw material, is extremely small, it is anticipated that it will become difficult to supply a sufficient amount of CPT as the demand of CPT-11, which is its effective derivative, increases, although means to procure the raw material including planting has been taken. Furthermore, since CPT-11 is prepared from a naturally-derived extract after isolation and purification, a difference in raw materials such as *Camptotheca acuminata* and *Nothapodytes foetida* may cause the inclusion of different impurities. Thus, when *Nothapodytes foetida* is used as the raw material, the extract contains 18,19-dehydrocamptothecin represented by a formula (1):

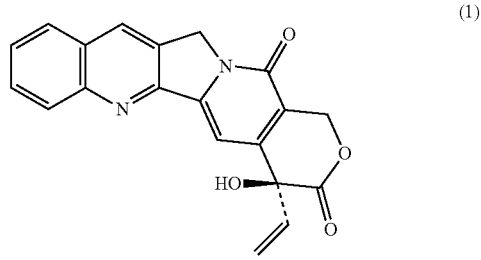 [SMILES: C=C[C@@]1(O)C(=O)OCc2c1cc1n(c2=O)Cc2cc3ccccc3nc2-1]

at a rate of several percent relative to CPT (refer to Patent document 1, Non-patent document 1). Regarding vinyl-form compounds having a vinyl group such as 18, 19-dehydro-camptothecin, the vinyl group remains in the subsequent production processes of CPT-11 as shown below, and the vinyl form cannot be completely removed by silica-gel column chromatography and others in any of the subsequent processes; therefore, it was difficult to obtain CPT-11 with high purity, when *Nothapodytes foetida* was used as the raw material.

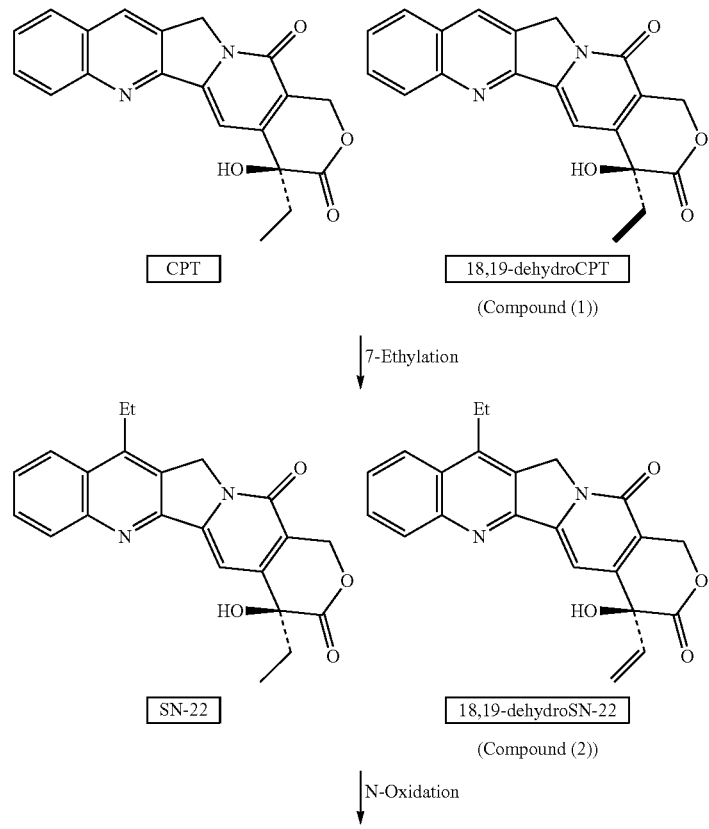

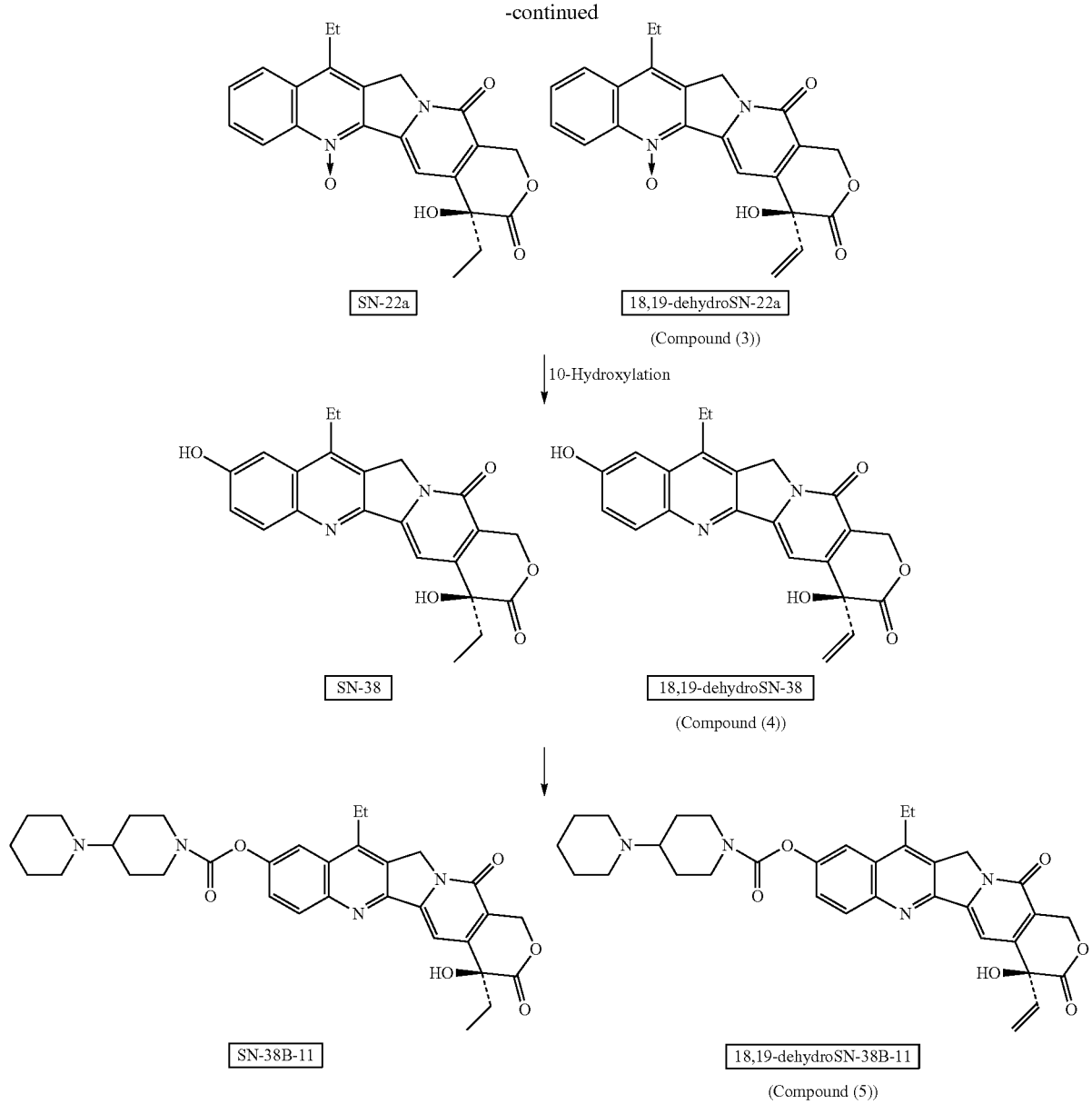

(Compound (3))

(Compound (4))

(Compound (5))

Meanwhile, the problem of impurities will be solved when total synthesis is used; however, the preparation process by total synthesis has many problems in terms of equipment, yield and cost, so that the practical application has not yet been achieved.

[Patent document 1] JP, A, 64-61482
[Non-patent document 1] R. Aiyama, et al., Phytochemistry, Vol. 27, No. 11, pp. 3663-3664, 1988.

DISCLOSURE OF THE INVENTION

Problem to be Solved by the Invention

Therefore, an object of the present invention is to provide a process for preparing 7-ethyl-10-[4-(1-piperidino)-1-piperidino]carbonyloxycamptothecin that does not comprise a vinyl form, from a camptothecin composition comprising 18,19-dehydrocamptothecin.

Means of Solving the Problem

During the present inventors' keen examination to solve the above-mentioned problem, they have found that, by the reduction under a certain condition of any one of the intermediates obtained by a process for preparing 7-ethyl-10-[4-(1-piperidino)-1-piperidino]carbonyloxycamptothecin from CPT, while a double bond and a carbonyl group within the heterocyclic ring of the CPT or 18,19-dehydrocamptothecin are not reduced but only a vinyl group is reduced, so that finally 7-ethyl-10-[4-(1-piperidino)-1-piperidino]carbonyloxycamptothecin that does not comprise a vinyl form can be prepared; the present invention has thus been accomplished.

Namely, the present invention relates to a process for preparing 7-ethyl-10-[4-(1-piperidino)-1-piperidino]carbonyloxycamptothecin from a composition comprising a compound represented by formula (1):

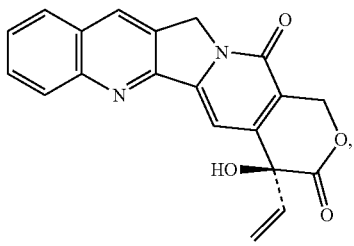

characterized in that in the process of producing a compound (2):

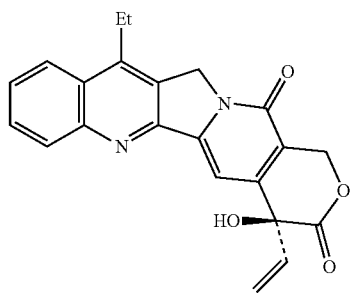

from the compound (1), then producing a compound (3):

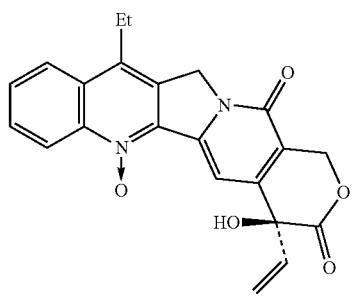

from the compound (2), then producing a compound (4):

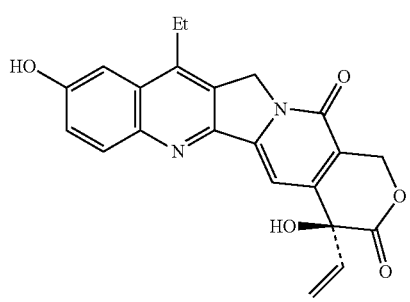

from the compound (3), and then producing a compound (5):

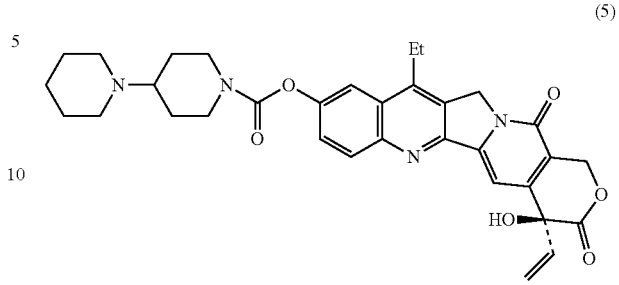

from the compound (4), at least one compound selected from the compounds (1)-(5) is catalytically reduced.

In addition, the present invention relates to said process for preparing 7-ethyl-10-[4-(1-piperidino)-1-piperidino]carbonyloxycamptothecin, characterized in that the compound (5) is catalytically reduced.

Furthermore, the present invention relates to said process for preparing 7-ethyl-10-[4-(1-piperidino)-1-piperidino]carbonyloxycamptothecin, wherein the composition comprising the compound (1) is a mixture with a compound (6):

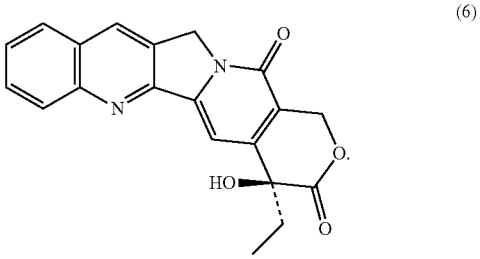 [SMILES: CC[C@@]1(O)C(=O)OCc2c1cc1n(c2=O)Cc2cc3ccccc3nc2-1]

In addition, the present invention relates to said process for preparing 7-ethyl-10-[4-(1-piperidino)-1-piperidino]carbonyloxycamptothecin, wherein the composition comprising the compound (1) is an extract of *Nothapodytes foetida*.

Furthermore, the present invention relates to said process for preparing 7-ethyl-10-[4-(1-piperidino)-1-piperidino]carbonyloxycamptothecin, wherein the catalytic reduction is performed under the presence of a catalyst using hydrogen or a formic acid or its salt as a hydrogen source.

Effects of the Invention

According to the inventive process, it becomes possible to use a camptothecin composition comprising 18,19-dehydrocamptothecin such as a *Nothapodytes foetida* extract, which is difficult to be used to date as a raw material of CPT-11, in the preparation of 7-ethyl-10-[4-(1-piperidino)-1-piperidino] carbonyloxycamptot hecin; the process exhibits extremely superior effects in terms of procurement of raw materials and improvement in product purities.

BEST MODE OF THE INVENTION

A process for preparing 7-ethyl-10-[4-(1-piperidino)-1-piperidino]carbonyloxycamptothecin according to the present invention is explained hereinbelow; however, the present invention is not limited thereto.

7-Ethyl-10-[4-(1-piperidino)-1-piperidino]carbonyloxycamptothecin is prepared from a camptothecin composition comprising 18,19-dehydrocamptothecin, by the following processes.

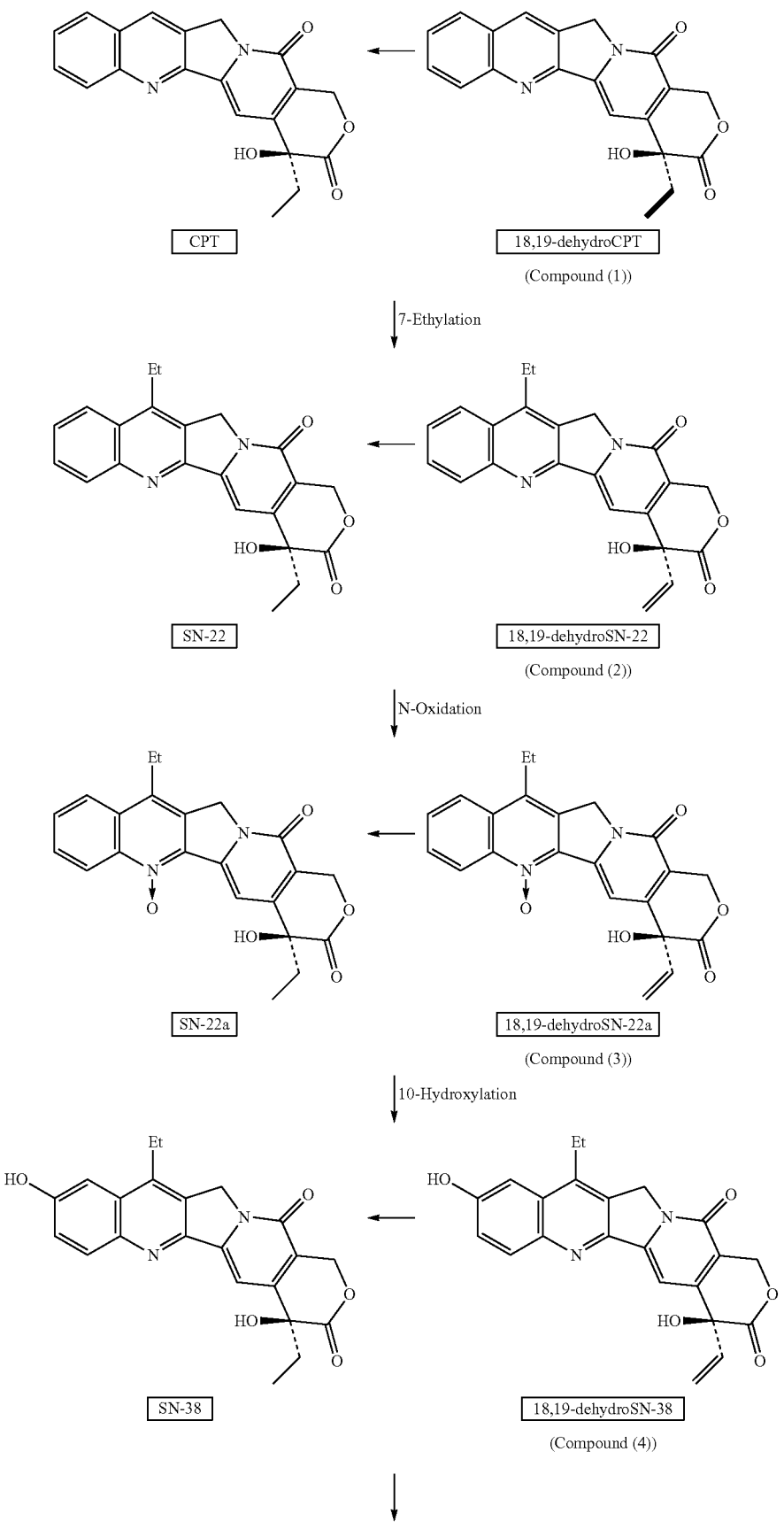

-continued

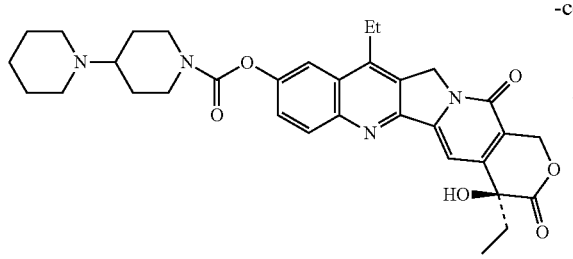

SN-38B-11

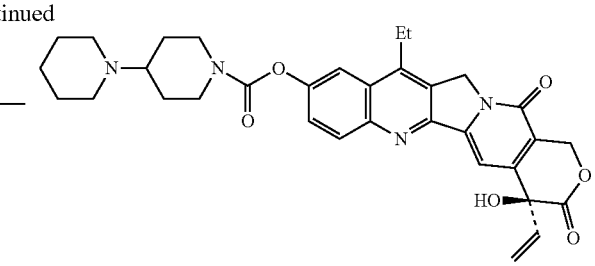

18,19-dehydroSN-38B-11
(Compound (5))

With respect to CPT that is a starting material as well as reaction conditions and others in each process, refer to JP A 62-42914, JP A 62-47193, JP A 3-68007 and WO 01/070747 which are incorporated herein by reference.

In the process of the present invention, by means of catalytically reducing any one of the above compounds (1)-(5), 7-ethyl-10-[4-(1-piperidino)-1-piperidino]carbonyloxy-camptothecin that does not comprise a vinyl form, and its hydrochloride trihydrate, i.e., CPT-11, can finally be prepared.

Compared to the compounds (1)-(4), the compound (5) has a higher solubility to a reaction medium so that the amount of the reaction medium can be reduced; therefore, catalytic reduction can be performed at a high concentration, thereby increasing reaction efficiency when the same amount of a catalyst is used, and the catalytic reduction can be completed within a shorter period. Thus, the reduction of the compound (5) is particularly preferred.

Catalytic reduction can be performed under the presence of a catalyst, using hydrogen or a formic acid or its salt as a hydrogen source. Examples of the catalyst used include platinum-group catalysts such as palladium, platinum, rhodium, ruthenium and the like, or nickel-group catalysts such as nickel and the like, or salts thereof; palladium, rhodium, ruthenium and nickel are preferred, and palladium is particularly preferred. In addition, examples of the formate used as a hydrogen source include ammonium formate, triethylammonium formate and the like; ammonium formate is preferred.

The use of ammonium formate is most preferred from the viewpoint of safety and handling.

The process of the present invention can be applied to any camptothecin composition comprising 18,19-dehydrocamptothecin; it is suitable for a 18,19-dehydrocamptothecin-containing composition extracted from *Nothapodytes foetida*.

EXAMPLES

The present invention is illustrated further in detail by reference to Examples.

Example 1

Catalytic reduction of 7-ethyl-10-[4-(1-piperidino)-1-piperidino]carbonyloxycamptothecin (SN-38B-11) that comprises 7-ethyl-10-[4-(1-piperidino)-1-piperidino]carbonyloxy-18,19-dehydrocamptothecin (18,19-dehydroSN-38B-11, compound (5))

A camptothecin comprising approximately 3% of 18,19-dehydrocamptothecin (compound (1)), which has been isolated and purified from Nothapodytes foetida, is prepared in accordance with the preparation process of SN-38B-11, giving a SN-38B-11 that comprises 18,19-dehydroSN-38B-11 (compound (5)).

The content of the vinyl form (compound (5)) in the SN-38B-11 obtained by isolation and purification is shown in Table 1 below.

TABLE 1

| | SN-38B-11 | | |
|---|---|---|---|
| Vinyl form | Sample 1 | Sample 2 | Sample 3 |
| (%) | 1.63 | 1.94 | 1.95 |

[Test Method]

The SN-38B-11 (100 mg) comprising the vinyl form (compound (5)) obtained by isolation and purification is dissolved in 20 mL of a dioxane-ethanol mixture solution (1:1) in a hydrogenation reaction vessel (100 mL), and approximately 10 mg of 10% Pd—C is added to the resultant mixture. Approximately 1.2 mL of the mixture is measured, filtered through a membrane filter (0.45 μm), and 1 mL of the filtrate is precisely measured, which is then made precisely to a volume of 10 mL by adding a dissolved solution [MeOH-$H_2O$-0.1 N HCl (5:4:1)]; thus, an initial sample solution is obtained. The reaction vessel is deaerated under reduced pressure and shaken under hydrogen atmosphere. At 30, 60, 120 and 240 min thereafter, approximately 1.2 mL of the sample is measured, filtered through a membrane filter (0.45 μm), and 1 mL of the filtrate is precisely measured, which is then made precisely to a volume of 10 mL by adding the dissolved solution; thus, a sample solution at each time point is obtained. Regarding 20 μL of each sample solution, the content of the vinyl form (compound (5)) in the reaction mixture is measured under the HPLC operating conditions described below.

[HPLC Operating Conditions]

Column: Inertsil ODS2, 5 μm, 4.6 mm×25 cm

Eluent: 20 mM PBS (pH 3.5)-MeOH-MeCN (3.5:1:1)

Detect: 254 nm

TABLE 2

| | SN-38B-11 | | |
|---|---|---|---|
| Time(min) | Sample 1 | Sample 2 | Sample 3 |
| 0 | 1.63 | 1.94 | 1.95 |
| 30 | 0.62 | 0.91 | 0.95 |
| 60 | 0.22 | 0.47 | 0.53 |

TABLE 2-continued

| | SN-38B-11 | | |
|---|---|---|---|
| Time(min) | Sample 1 | Sample 2 | Sample 3 |
| 120 | 0.08 | 0.12 | 0.15 |
| 240 | ND | ND | ND |

% peak area

After the above-described reaction, no vinyl form (compound (5)) was detected in any sample at 240 min after.

Example 2

Catalytic reduction of 7-ethyl-10-[4-(1-piperidino)-1-piperidino]carbonyloxycamptothecin (SN-38B-11) that comprises 7-ethyl-10-[4-(1-piperidino)-1-piperidino]carbonyloxy-18,19-dehydrocamptothecin (18,19-dehydroSN-38B-11, compound (5))

Catalytic reduction was performed using ammonium formate as the hydrogen source instead of hydrogen gas.
[Test Method]
Crude SN-38B-11 was added and dissolved into methanol (60 v/w) and dioxane (15 v/w), and Pd—C (10%) (dry matter equivalent: 0.05, 0.05, 0.10 w/w) suspended in filtered water (approximately 0.2 w/w) was added to the resultant solution, which was then reacted by adding an ammonium formate (0.50, 1.00, 1.00 w/w); the content of the vinyl form (compound (5)) in the reaction mixture at 1, 2, 3 and 4 h after the reaction was measured by HPLC. Table 3 shows the results.
[HPLC Operating Conditions]
Column: Chemcosorb 5-ODS-H, 4.6 mm ID×150 mm
Eluent: 0.1% (v/v) phosphoric acid/$CH_3CN$(4/1)
Detect: 254 nm
Temperature: 40° C.
Flow rate: 1 mL/min

TABLE 3

| Experiment No. | 92-011 | 92-012 | 92-017 |
|---|---|---|---|
| Pd-C (10%) dry matter equivalent (w/w) | 0.05 | 0.05 | 0.10 |
| Ammonium formate (w/w) | 0.50 | 1.00 | 1.00 |
| Vinyl form (compound (5)) before reaction | 1.05% | 1.05% | 0.74% |
| Reaction time (hr) | | | |
| 1 | 0.64%* | 0.22% | ND |
| 2 | 0.44% | 0.05% | ND |
| 3 | 0.38% | 0.01% | ND |
| 4 | 0.37% | — | — |

*% peak area of vinyl form

By using 0.10 w/w of Pd—C (10%) (relative to the crude SN-38B-11) and 1.00 w/w of ammonium formate, the reaction was completed in 60-180 min.

Example 3

Catalytic Reduction of Camptothecin (CPT) that Comprises 18,19-dehydrocamptothecin (18,19-dehydroCPT, Compound (1))

SN-38B-11 is prepared from a camptothecin comprising 18,19-dehydrocamptothecin (compound (1)) isolated from *Nothapodytes foetida*, in accordance with the preparation process of SN-38B-11, so that SN-22, SN-22a, and SN-38 that respectively comprise an intermediate 18,19-dehydroSN-22 (compound (2)), 18,19-dehydroSN-22a (compound (3)), and 18,19-dehydroSN-38 (compound (4)) are obtained.

The contents of the vinyl form (compound (1), compound (2), compound (3), and compound (4)) in CPT, SN-22, SN-22a and SN-38 used in the test are shown in Table 4.
[Test Method]
The CPT (100 mg) comprising the vinyl form (compound (1)) is dissolved in 200 mL of a dioxane-methanol mixture solution (1:1) in a recovery flask, and approximately 20 mg of 10% Pd—C is added to the resultant mixture. Approximately 1 mL of the mixture is measured and filtered through a membrane filter (0.45 μm), giving an initial sample solution. The reaction vessel is deaerated under reduced pressure and vigorously stirred under hydrogen atmosphere at room temperature. At 1, 3, and 5 hr thereafter, approximately 1 mL of the sample is measured and filtered through a membrane filter (0.45 μm), giving a sample solution at each time point. Regarding 20 μL of each sample solution, the content of the vinyl form (compound (1)) in the reaction mixture is measured under the HPLC operating conditions described below.

Table 4 shows the experimental results. No vinyl form (compound (1)) was detected at 5 hr after.
[HPLC Operating Conditions]
Column: Chemcosorb 5-ODS-H, 4.6 mm ID×150 mm
Temperature: 40° C.
Eluent: Methanol/0.10 (v/v) phosphoric acid (53/47) mixture solution
Detect: 254 nm
Flow rate: 0.8 mL/min Example 4

Catalytic reduction of 7-ethylcamptothecin (SN-22) that comprises 7-ethyl-18,19-dehydrocamptothecin (18,19-dehydroSN-22, compound (2))

[Test Method]
The SN-22 (100 mg) comprising the vinyl form (compound (2)) is dissolved in 100 mL of a dioxane-ethanol mixture solution (1:1) in a recovery flask, and approximately 10 mg of 10% Pd—C is added to the resultant mixture. Approximately 1 mL of the mixture is measured and filtered through a membrane filter (0.45 μm), giving an initial sample solution. The reaction vessel is deaerated under reduced pressure and vigorously stirred under hydrogen atmosphere at room temperature. At 1, 3, 5 and 7 hr thereafter, approximately 1 mL of the sample is measured and filtered through a membrane filter (0.45 μm), giving a sample solution at each time point. Regarding 10 μL of each sample solution, the content of the vinyl form (compound (2)) in the reaction mixture is measured under the HPLC operating conditions of Example 3.

Table 4 shows the experimental results. No vinyl form (compound (2)) was detected at 7 hr after.

Example 5

Catalytic reduction of 7-ethylcamptothecin N-oxide (SN-22a) that comprises 7-ethyl-18,19-dehydrocamptothecin N-oxide (18,19-dehydroSN-22s, compound (3))

[Test Method]
With respect to the SN-22a (100 mg) comprising the vinyl form (compound (3)), a sample solution is prepared and collected by the catalytic reduction process similar to that in Example 4, and the content of the vinyl form (compound (3)) in the reaction mixture is measured under the HPLC operating conditions shown below.

Table 4 shows the experimental results. No vinyl form (compound (3)) was detected at 7 hr after.

[HPLC Operating Conditions]
Column: Chemcosorb 5-ODS-H, 4.6 mm ID×150 mm
Temperature: 35° C.
Eluent: Methanol/0.1% (v/v) phosphoric acid (53/47) mixture solution
Detect: 254 nm
Flow rate: 0.8 mL/min Example 6

Catalytic reduction of 7-ethyl-10-hydroxycamptothecin (SN-38) that comprises 7-ethyl-10-hydroxy-18, 19-dehydrocamptothecin (18,19-dehydroSN-38, compound (4))

[Test Method]

The SN-38 (100 mg) comprising the vinyl form (compound (4)) is dissolved in 40 mL of a dioxane-methanol mixture solution (1:1) in a recovery flask, and approximately 20 mg of 10% Pd—C and 0.15 mL of water are added to the resultant mixture. Approximately 0.5 mL of the mixture is measured and filtered through a membrane filter (0.45 μm), giving an initial sample solution. Ammonium formate (100 mg) is added to this mixture and vigorously stirred at room temperature. At 1 and 3 hr thereafter, approximately 0.5 mL of the sample is measured and filtered through a membrane filter (0.45 μm), giving a sample solution at each time point. Regarding 4 μL of each sample solution, the content of the vinyl form (compound (4)) in the reaction mixture is measured under the HPLC operating conditions of Example 3.

Table 4 shows the experimental results. No vinyl form (compound (4)) was detected at 3 hr after.

TABLE 4

| Reaction Time(hr) | Content of vinyl form (%) | | | |
|---|---|---|---|---|
| | Compound (1) | Compound (2) | Compound (3) | Compound (4) |
| 0 | 1.41 | 1.25 | 1.13 | 1.06 |
| 1 | 0.73 | 0.52 | 0.59 | 0.11 |
| 3 | 0.18 | 0.12 | 0.18 | ND |
| 5 | ND | 0.02 | 0.16 | — |
| 7 | — | ND | ND | — |

Reference Test

Removal of 7-ethyl-10-[4-(1-piperidino)-1-piperidino] carbonyloxycamptothecin (SN-38B-11) that comprises 7-ethyl-10-[4-(1-piperidino)-1-piperidino]carbonyloxy-18, 19-dehydrocamptothecin (18,19-dehydroSN-38B-11, compound (5)) by means of silica gel chromatography Regarding 200 mg of the sample 1 in Table 1, Table 5 shows the fractionation by column chromatography using silica gel with an amount approximately 150 times and its analytical results.

[Test Method]

The sample 1 is charged on a silica gel column (Merck Silica Gel 60, 230-400 mesh ATMS, 2×10 cm, approximately 30 g) and is flown down with a CHCl$_3$-MeOH (20:1) mixture solution (10 mL/min). The flowing-down solution is fractionated by 30 mL. Each fraction is concentrated to dryness under reduced pressure, and the residue is dissolved into a dissolving solution to achieve the concentration of 1 mg/mL, giving a sample solution. 10 μL of the sample solution is tested under the HPLC operating conditions shown below.

Dissolving solution: MeOH-H$_2$O-0.1 N HCl (5:4:1)
[HPLC Operating Conditions]
Column: Inertsil ODS2, 5 μm, 4.6 mm×25 cm
Eluent: 20 mM PBS (pH 3.5)-MeOH-MeCN (3.5:1:1)
Detect: 254 nm

TABLE 5

| | Vinyl form | | |
|---|---|---|---|
| Fr. No. | (g) | (compound (5))(%) | SN-38B-11(%) |
| 1 | 0.05 | 0.36 | 97.33 |
| 2 | 0.05 | 0.76 | 98.62 |
| 3 | 0.03 | 1.36 | 98.16 |
| 4 | 0.02 | 2.17 | 97.62 |
| 5 | 0.02 | 2.47 | 97.25 |
| 6 | 0.01 | 2.52 | 97.23 |
| 7 | 0.01 | 2.79 | 96.81 |
| 8 | 0.01 | 2.76 | 96.62 |

% peak area

The contents of the vinyl form increased at the latter portions of the SN-38B-11 fractions. The removal of the vinyl form was therefore difficult under these operating conditions.

The invention claimed is:

1. A method for preparing 7-ethyl-10[4-(1-piperidino)-1-piperidino]carbonyloxycamptothecin comprising:
treating a composition comprising 7-ethyl-10[4-(1-piperidino)-1-piperidino]carbonyloxycamptothecin and a compound represented by formula (5):

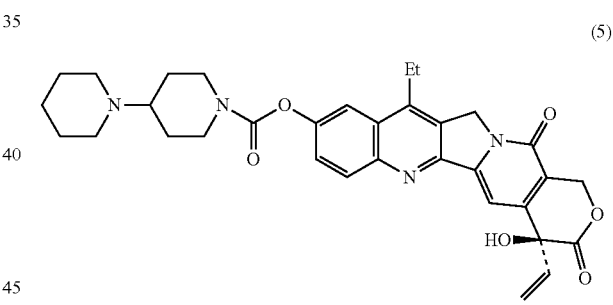

(5)

with a catalyst and hydrogen or a formic acid or its salt as a hydrogen source, such that compound (5) is catalytically reduced to form 7-ethyl-10[4-(1-piperidino)-1-piperidino]carbonyloxycamptothecin, and compound (5) is not detectable under standard HPLC conditions following catalytic reduction.

2. The method of claim 1, wherein the composition comprising 7-ethyl-10-[4-(1-piperidino)-1-piperidino]carbonyloxycamptothecin and compound (5) is derived from a camptothecin composition isolated from *Nothapodytes foetida*.

3. The method of claim 1, wherein the composition contains about 0.74% to about 1.95% of compound (5).

4. The method of claim 1, wherein the catalyst is 10% Pd-C.

5. The method of claim 1, wherein the hydrogen source is hydrogen gas.

6. The method of claim 1, wherein the hydrogen source is ammonium formate.

* * * * *

UNITED STATES PATENT AND TRADEMARK OFFICE
CERTIFICATE OF CORRECTION

| | |
|---|---|
| PATENT NO. | : 8,476,438 B2 |
| APPLICATION NO. | : 12/226506 |
| DATED | : July 2, 2013 |
| INVENTOR(S) | : Seigo Sawada et al. |

It is certified that error appears in the above-identified patent and that said Letters Patent is hereby corrected as shown below:

In the Claims:

Claim 1, column 14, line 28, should read:

1. A method for preparing 7-ethyl-10-[4-(1-piperidino)-1-piperidino]carbonyloxycamptothecin comprising:

treating a composition comprising 7-ethyl-10-[4-(1-piperidino)-1-piperidino]carbonyloxycamptothecin and a compound represented by formula (5):

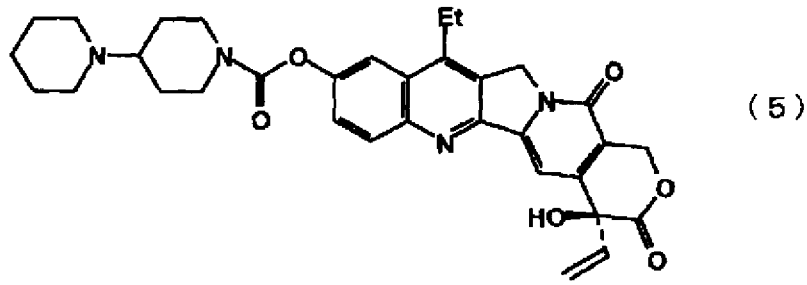

with a catalyst and hydrogen or a formic acid or its salt as a hydrogen source, such that compound (5) is catalytically reduced to form 7-ethyl-10-[4-(1-piperidino)-1-piperidino]carbonyloxycamptothecin, and compound (5) is not detectable under standard HPLC conditions following catalytic reduction.

Signed and Sealed this
Twelfth Day of November, 2013

Teresa Stanek Rea
*Deputy Director of the United States Patent and Trademark Office*